US006814931B2

(12) United States Patent
Kaiser

(10) Patent No.: US 6,814,931 B2
(45) Date of Patent: Nov. 9, 2004

(54) METHOD AND APPARATUS FOR TREATING AN OBJECT WITH OZONE

(75) Inventor: Herbert J. Kaiser, Pontoon Beach, IL (US)

(73) Assignee: Steris Inc., Temecula, CA (US)

( * ) Notice: Subject to any disclaimer, the term of this patent is extended or adjusted under 35 U.S.C. 154(b) by 90 days.

(21) Appl. No.: 10/326,484

(22) Filed: Dec. 20, 2002

(65) Prior Publication Data

US 2004/0120850 A1 Jun. 24, 2004

(51) Int. Cl.$^7$ ................................................ A61L 2/00
(52) U.S. Cl. .................... 422/22; 250/455.11; 422/24; 422/186.01; 422/186.1
(58) Field of Search .................... 422/22, 24, 186.01, 422/186.1; 250/455.11

(56) References Cited

U.S. PATENT DOCUMENTS

| | | | | |
|---|---|---|---|---|
| 3,941,670 A | * | 3/1976 | Pratt, Jr. ................ | 204/157.61 |
| 4,265,747 A | * | 5/1981 | Copa et al. .................. | 210/758 |
| 4,606,471 A | * | 8/1986 | Quercetti ..................... | 220/555 |
| 4,609,471 A | * | 9/1986 | Beemster et al. ............ | 210/748 |
| 4,978,508 A | * | 12/1990 | Hansen et al. .......... | 422/186.08 |
| 5,586,134 A | | 12/1996 | Das et al. ...................... | 372/38 |
| 5,730,934 A | * | 3/1998 | Holbert ........................ | 422/24 |
| 6,056,918 A | * | 5/2000 | Palaniappan et al. .......... | 422/24 |
| 6,379,613 B1 | | 4/2002 | Stempf ......................... | 422/26 |
| 6,461,487 B1 | | 10/2002 | Andrews et al. ............ | 204/262 |
| 6,468,953 B1 | | 10/2002 | Hitchems et al. ........... | 510/218 |

OTHER PUBLICATIONS

U.S. patent application Ser. No. 60/375,851 filed Apr. 24, 2002, McVey et al., entitled: Activated Oxidizing Vapor Treatment System and Method.
Article entitled: "*The Shape of Lights to Come*," Siemens AG Webzine Archives—Research and Innovation, Jan. 2000, 4 pages.
Press Release entitles: "*Highly efficient VUV and ozone production system from OSRAM*," OSRAM Sylvania, Jul. 23, 2002, 2 pages.
USHIO Product Specification Sheet, UER200–172 Excimer UV lamp–house, OSHIO America, Incorporated.
U.S. patent application Ser. No. 10/422,474, filed Apr. 24, 2003, McVey et al., entitled: Activated Oxidizing Vapor Treatment System and Method.

* cited by examiner

Primary Examiner—Krisanne Jastrzab
(74) Attorney, Agent, or Firm—Kusner & Jaffe; Michael A. Centanni

(57) ABSTRACT

A treatment system for treating objects (e.g., medical instruments) with ozone gas. The ozone treatment system includes a treatment tank wherein the objects are exposed to ozone. In a preferred embodiment, the ozone is generated within the treatment tank by exposing an oxygen-containing gas to ultraviolet radiation produced by a laser.

17 Claims, 3 Drawing Sheets

METHOD AND APPARATUS FOR TREATING AN OBJECT WITH OZONE

FIELD OF THE INVENTION

The present invention relates generally to the field biocontamination inactivation and destruction, and more particularly to a method and apparatus for treating an object with ozone.

BACKGROUND OF THE INVENTION

Ozone is a form of oxygen that has three atoms per molecule rather than two atoms as found in molecular oxygen. Ozone ($O_3$) rapidly decomposes into molecular oxygen ($O_2$), as the "extra" oxygen atom splits off the ozone molecule. This "extra" oxygen atom is known to inactivate bacteria, spores and react with chemical compounds. Consequently, disinfection and oxidation occur. Ozone has been recognized to inactivate many known biological contaminants, chemical contaminants and infectious agents. These infectious agents include, but are not limited to, bacteria, viruses and prions.

Prions are infectious agents that recently have been the subject of significant scientific research. Prions can be defined as small proteinaceous infectious particles which resist inactivation by procedures that modify nucleic acids. Prions have a pleated sheet conformation rather than a helix structure that is normal for prion protein, lack detectable nucleic acid, and do not elicit an immune response. Prions are now believed to be responsible for several transmissible neurodegenerative diseases, such as Creutzfeldt-Jakob disease (CJD) and kuru in humans, scrapie in sheep, and mad-cow disease (bovine spongiform encephalopathy (BSE)) in cattle. Inactivating prions using heat, radiation, enzymes, and cleaving chemicals appears to have been unsuccessful. It is believed that ozone has the capability to potentially inactivate prions by destruction and/or removal thereof.

The present invention provides a method and apparatus for ozone treatment of an object, including, but not limited to surgical instruments.

SUMMARY OF THE INVENTION

In accordance with the present invention, there is provided an apparatus for treating an object with ozone, comprising: (a) a treatment tank having a sealable inner chamber; (b) at least one reflective surface located within the inner chamber; (c) an oxygen-containing gas within said inner chamber; and (d) a laser for emitting a laser beam of ultraviolet (UV) radiation through the inner chamber, said laser beam reflected by the reflective surface, wherein exposure of the oxygen-containing gas to the UV radiation produces ozone.

In accordance with another aspect of the present invention, there is provided a method for treating an object with ozone, comprising the steps of: (a) placing the object within a sealed chamber containing an oxygen-containing gas; and (b) introducing ultraviolet radiation into the chamber, wherein oxygen of the oxygen-containing gas produces ozone gas.

An advantage of the present invention is the provision of a method and apparatus for treating objects with ozone, wherein a laser is used to produce large quantities of ozone gas within a treatment tank.

Another advantage of the present invention is the provision of a method and apparatus for treating objects with ozone that produces sufficient quantities of ozone to effectively inactivate infectious agents, such as prions.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

Figure 1:
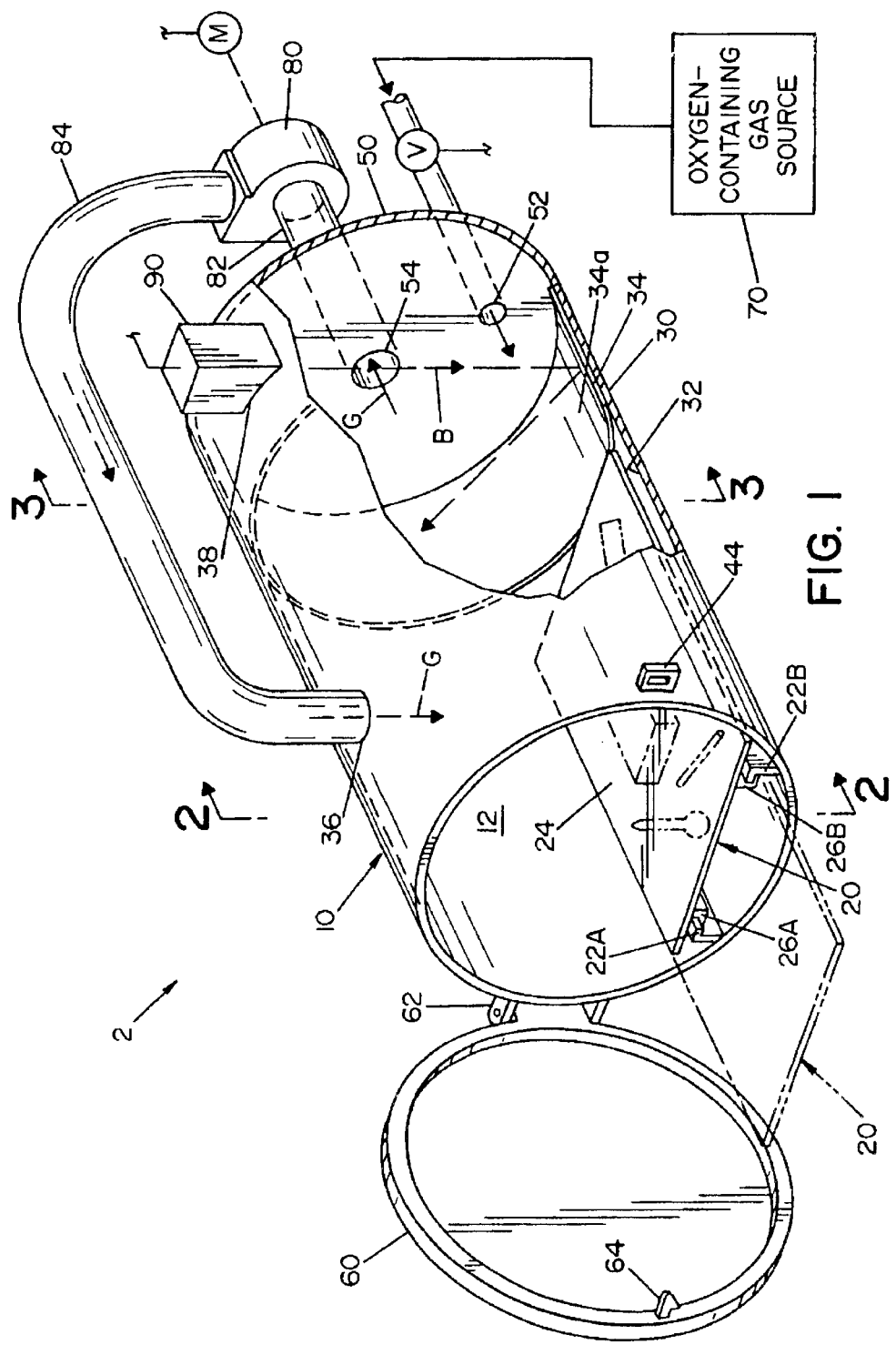
FIG. 1 is a perspective view of an ozone treatment system, according to a preferred embodiment of the present invention.

Referring now to the drawings wherein the showings are for the purposes of illustrating a preferred embodiment of the invention only and not for purposes of limiting same, FIG. 1 shows an ozone treatment system 2, according to a preferred embodiment of the present invention. Ozone treatment system 2 is generally comprised of a treatment tank 10, an oxygen-containing gas source 70, a blower 80, and a laser 90 that emits a laser beam B. Objects located within treatment tank 10 are exposed to ozone gas. The ozone gas is produced within treatment tank 10 by passing the laser beam through an ozone-containing gas. Blower 80 circulates the ozone-containing gas and ozone throughout treatment tank 10. Operation of ozone treatment system 2 is described in greater detail below.

In a preferred embodiment, treatment tank 10 is generally comprised of a tank body 30, a rear wall 50, and a door 60. Rear wall 50 is located at the rear end of tank body 30. Door 60 is located at the front end of tank body 30. An inner chamber 12 is defined by tank body 30, rear wall 50 and door 60. Door 60 seals an opening into inner chamber 12. In a preferred embodiment, tank body 30, rear wall 50 and door 60 may form a pressurizable vessel. Accordingly, these elements are preferably formed of a pressurizable material, such as a metal (e.g., stainless steel).

Figure 2:
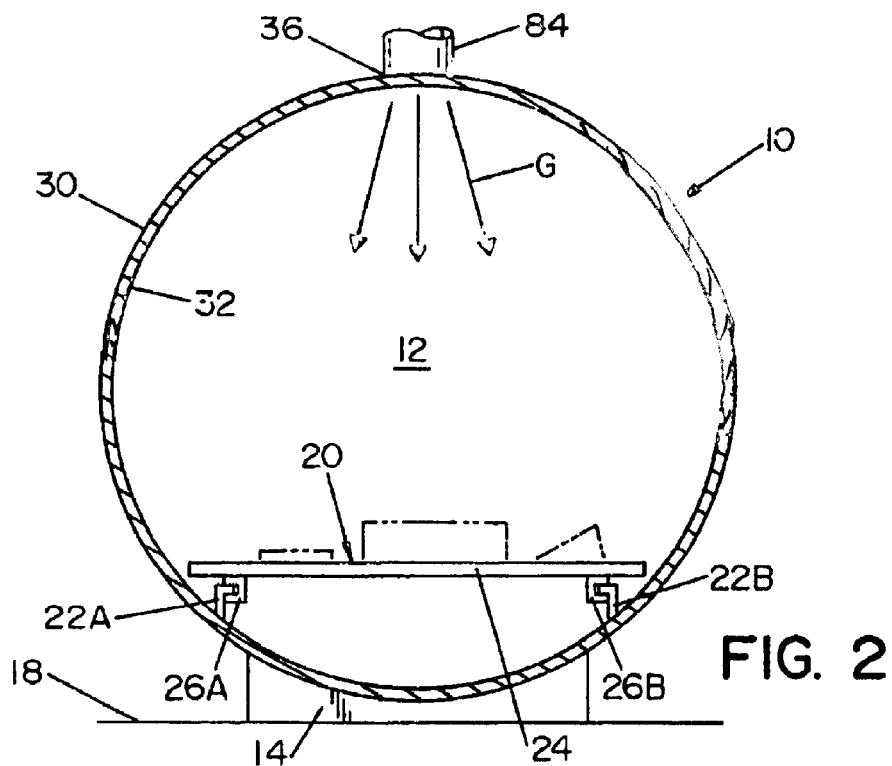
FIG. 2 is a cross-sectional view of the ozone treatment system, taken along lines 2—2 of FIG. 1.

Tank body 30 is a generally cylindrical wall having a circular cross-section. The cross-section of tank body 30 may have alternative geometries, including an oval. Tank body 30 defines an inner surface 32. A base 14 supports tank body 30 on a generally planar surface 18 (see FIGS. 2 and 3).

Figure 3:
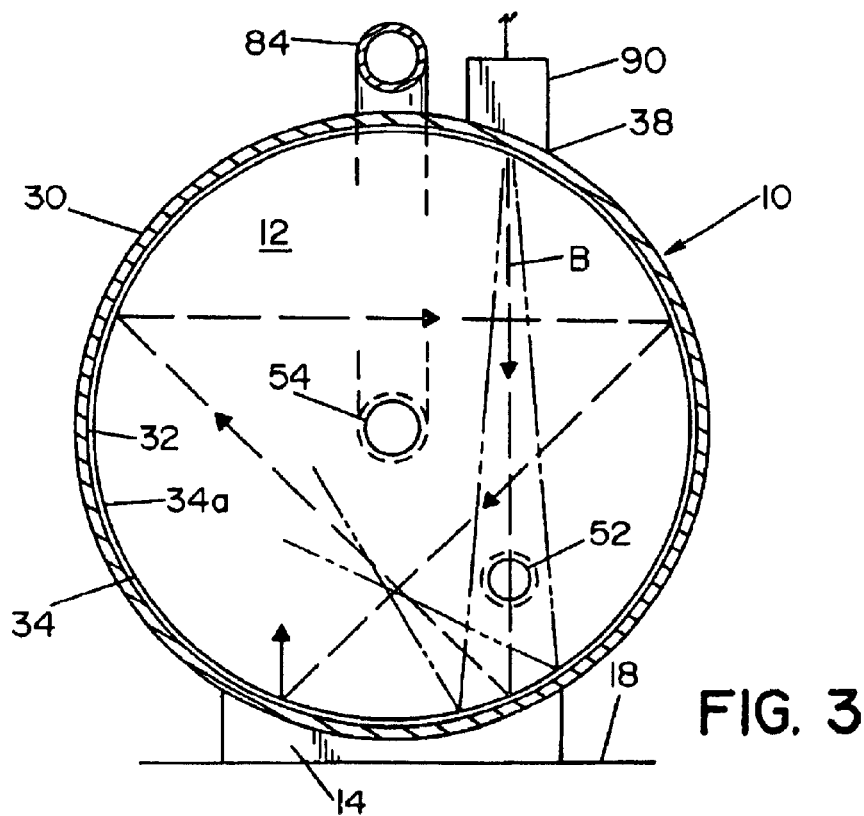
FIG. 3 is a cross-sectional view of the ozone treatment system, taken along lines 3—3 of FIG. 1.

At least one reflective element 34 is located within inner chamber 12. Reflective element 34 includes a reflective surface 34a that reflects laser beam B emitted by laser 90, as will be described in detail below. Reflective element 34 may take many suitable forms. In a preferred embodiment, reflective element 34 takes the form of a reflective coating material applied to at least a portion of inner surface 32 (FIGS. 1 and 3). By way of example, and not limitation, the reflective coating material may be a thin gold film applied to at least a portion of inner surface 32. In fact, any metal that can be deposited so as to produce a reflective surface and not adversely interact with ozone may be used. For example, metals such as molybdenum, tungsten, palladium, zirconium, yttrium, and tantalum can be used as a reflective coating material.

In an alternative embodiment, reflective element 34 is formed by polishing at least a portion of inner surface 32, to provide a mirror-like reflective surface. In yet another alternative embodiment, shown in FIG. 4, reflective element 34 takes the form of a one or more reflective members 110 mounted to at least a portion of inner surface 32. Each reflective member 110 has a curved or flat mirrored reflective surface 112. It should be appreciated that two or more of the various types of reflective elements 34 described above may be used in combination, and may be located in one or more regions of inner chamber 12. In a preferred embodiment, reflective element 34 provides specular reflection. It should also be appreciated that it may be advantageous to use a reflective element 34 that provides diffuse reflection of laser beam B. This would spread laser beam B throughout inner chamber 12, thereby creating a large quantity of ozone.

It should be appreciated that the path of laser beam B is preferably maintained to avoid direct contact with the object being treated. To this end, reflective element 34 may be located within a selected region of inner chamber 12 to reflect laser beam B only within that selected region. In the embodiment illustrated in FIG. 1, the selected region is located in the rear portion of inner chamber 12. Ozone generated in the selected region is circulated into other regions of inner chamber 12 by blower 80 (described below). In particular, ozone is circulated into a region of inner chamber 12, where the objects being treated are located.

Rear wall 50 and door 60 are located at opposite ends of tank body 30. Door 60 is attached to tank body 30 at the open end thereof. Door 60 seals the open end of tank body 30, as indicated above. In a preferred embodiment, a hinge 62 attaches door 60 to tank body 30. A hook 64 on door 60 mates with a catch 44 on tank body 30 to secure a seal between door 60 and tank body 30. Door 60 allows convenient access to inner chamber 12 for loading and unloading of objects within inner chamber 12.

Oxygen-containing gas source 70 provides a supply of oxygen-containing gas to inner chamber 12. In this regard, a first inlet 52, formed in rear wall 50, provides an opening for receiving the oxygen-containing gas into inner chamber 12. A gas valve V controls the flow of oxygen-containing gas into inner chamber 12. In a preferred embodiment, oxygen-containing gas source 70 may take the form of a pressurized gas tank containing, by way of example, and not limitation, air or pure $O_2$.

Blower 80 circulates gases within inner chamber 12. Blower 80 is powered by a motor M. In a preferred embodiment, blower 80 is a circulating fan. Pipes 82 and 84 provide conduits for blower 80. A first outlet 54 is formed in rear wall 50 to provide an opening dimensioned to receive pipe 82. A second inlet 36 is formed in tank body 30 to provide an opening dimensioned to receive pipe 84. In a preferred embodiment, a gas G is drawn from inner chamber 12 into blower 80 through pipe 82. Gas G is then passed out of blower 80 through pipe 84. Accordingly, blower 80 circulates gas G through inner chamber 12.

Laser 90 is mounted to tank body 30. A third inlet 38 is formed in tank body 30 to provide an opening dimensioned to allow passage of laser beam B of laser 90 into inner chamber 12. Laser beam B is projected outward through a laser window (not shown) of laser 90, and into inner chamber 12, via inlet 38. Within inner chamber 12, laser beam B is reflected by reflective element 34. A detailed description of the operation of laser 90 is provided below.

It should be appreciated that laser 90 may include a beam sweep system (not shown) for sweeping laser beam B in a direction perpendicular or parallel to the longitudinal axis of tank body 30. Sweeping laser beam B may facilitate passing laser beam B through the oxygen-containing gas within inner chamber 12.

Laser 90 is preferably selected from those lasers that emit radiation having a wavelength in the ultraviolet (UV) region of the electromagnetic spectrum (i.e., wavelengths from about 40 to 400 nanometers), including, but not limited to, excimer lasers, nitrogen lasers, and third harmonic Neodymium: Yttrium Aluminum Garnet (Nd:YAG) lasers. In a preferred embodiment, laser 90 takes the form of an excimer laser, such as those available from USHIO America, Inc. Excimer lasers use a gas (e.g., xenon, krypton, argon, and neon gas) to form an "excited dimer," and thus produce a narrow band light (i.e., "laser beam") around a single wavelength (e.g., 126 nm, 146 nm, 172 nm, 222 nm, 282 nm, and 308 nm). In a preferred embodiment, xenon (Xe) gas is used to produce a laser beam B of ultraviolet radiation having a wavelength of 172 nm.

An object support assembly 20 is provided within inner chamber 12. Object support assembly 20 is basically comprised of a pair of generally parallel tracks 22A and 22B, a slidable support platform 24, and guides 26A and 26B. In a preferred embodiment, support platform 24 provides a generally planar surface for supporting objects within inner chamber 12 during ozone treatment. Guides 26A and 26B respectively engage with tracks 22A and 22B. In this regard, support platform 24 is reciprocally moveable along tracks 22A, 22B. Object support assembly 20 facilitates loading and unloading of objects within inner chamber 12. In this regard, support platform 24 is movable between a first position within inner chamber 12, and a second position outside of inner chamber 12, convenient for loading and unloading objects. In a preferred embodiment, support platform 24 is located within inner chamber 12 in a region axially offset from the path of laser beam B.

It should be appreciated that a conventional ozone sensor (not shown), well known to those skilled in the art, may be located within inner chamber 12 to detect the amount of ozone therein. Preferably, the ozone sensor is located at the end of inner chamber 12 farthest from the path of laser beam B. Accordingly, the ozone sensor can be used to detect the ozone level at the end of inner chamber 12 furthest from the source of ozone generation. For example, the ozone sensor could be suitably located at the inner surface of door 60.

A control unit (not shown) is used to control operation of valve V associated with ozone-containing gas source 70, motor M associated with blower 80, and laser 90. Furthermore, the control unit may receive data from the ozone sensor indicative of ozone levels within inner chamber 12. Control unit may be programmed to monitor the ozone levels indicated by the ozone sensor, and adjust operating parameters of valve V, motor M and laser 90 accordingly. In a preferred embodiment, control unit takes the form of a programmable microcontroller, or a personal computer (PC).

Operation of ozone treatment system 2 will now be described in detail. First, door 60 is moved to an open position to allow access to inner chamber 12. Support platform 24 is then slid from its first position to its second position, such that at least a portion of support platform 24 extends outside inner chamber 12 (as shown in phantom in FIG. 1). One or more objects to be treated are placed onto support platform 24. The objects may include, but are not limited to, medical instruments, mail that has been contaminated with biocontamination, and the like. Support platform 24 is then returned to its first position, wherein support platform 24 is fully received within inner chamber 12. Door 60 is then moved to a closed position to seal inner chamber 12.

Valve V is opened, and an oxygen-containing gas is released into inner chamber 12 through inlet 54.

Consequently, inner chamber 12 fills with the oxygen-containing gas.

In an alternative embodiment, air located within inner chamber 12 is used as the sole source of oxygen-containing gas. Accordingly, in this alternative embodiment, valve V remains closed.

Figure 4:
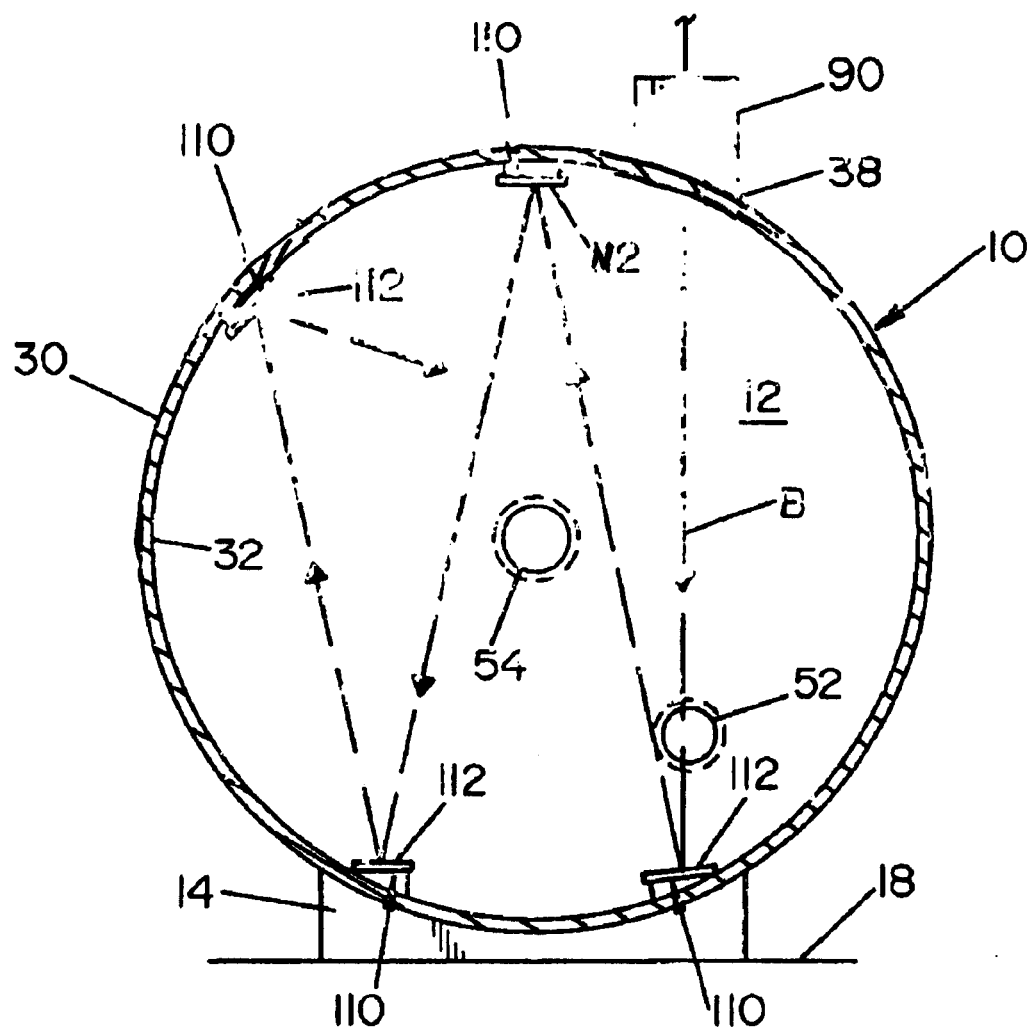
FIG. 4 is a cross-sectional view of an ozone treatment system, according to an alternative embodiment of the present invention.

Laser 90 is powered to generate laser beam B that is emitted through inlet 38 (FIG. 3). When laser beam B strikes the reflective element 34, laser beam B is reflected in accordance with the law of reflection (i.e., the angle of incidence is equal to the angle of reflection), as illustrated in FIGS. 3 and 4. If reflective element 34 has a smooth surface, then "specular" reflection occurs. If reflective element 34 has a rough surface, then "diffuse" reflection occurs. In a preferred embodiment, the path of laser beam B is limited to the region of inner chamber 12 having reflective element 34. One or more reflective elements 34 are arranged so as to maintain the path of the reflected laser beam B in a manner that avoids direct contact with the object(s).

Oxygen-containing gas (supplied by oxygen-containing gas source 70) located in the path of laser beam B, is exposed to the ultraviolet radiation of laser beam B. The ultraviolet radiation splits oxygen ($O_2$) molecules of the oxygen-containing gas to produce molecular ozone.

Blower 80 is activated by powering motor M. Blower 80 facilitates circulation of the ozone gas throughout inner chamber 12. Blower 80 also facilitates the circulation of the oxygen-containing gas into the path of the laser beam B. Exposure of the oxygen-containing gas to laser beam B produces ozone. It should be understood that blower 80 may be activated prior to activation of laser 90. The ozone oxidizes biocontaminants on the objects, including, but not limited to prions. It is believed that the oxidation process is facilitated by producing the ozone in very close proximity (in-situ) to the surface of the objects being treated. Reflection of laser beam B by reflective element 34 enlarges the path of laser beam B, thus allowing ozone to be generated throughout a large volume of inner chamber 12.

After the objects have been exposed to a sufficient quantity of ozone, valve V is closed, and laser 90 and motor M are deactivated. Door 60 is then opened and the objects can be unloaded from support platform 24. As indicated above, an ozone sensor may be used to measure ozone levels in inner chamber 12, and to determine whether the objects have been exposed to a sufficient quantity of ozone to effect activation of any biocontamination.

Other modifications and alterations will occur to others upon their reading and understanding of the specification. For instance, the laser and oxygen-containing gas source could be replaced with an ozone generator and pump to feed ozone directly into the inner chamber of the treatment tank. Furthermore, the laser could be selected to have a window large enough that it would be unnecessary to use a round or oval shaped treatment tank. In this regard, a larger window would result in a broader laser beam. Such a broader laser beam could be directed along the length of a tank, thereby creating ozone as it traverses the tank. It is intended that all such modifications and alterations be included insofar as they come within the scope of the invention as claimed or the equivalents thereof.

Having described the invention, the following is claimed:

1. An apparatus for treating an object with ozone, comprising:

a treatment tank having a sealable inner chamber, said object located within said inner chamber;

an oxygen-containing gas within said inner chamber;

a laser for emitting a laser beam of ultraviolet (UV) radiation through the inner chamber, wherein exposure of the oxygen-containing gas to the UV radiation produces ozone; and at least two reflective surfaces located within the inner chamber to reflect said laser beam along multiple paths through said inner chamber, said multiple paths avoiding contact with said object located within said inner chamber.

2. An apparatus as defined by claim 1, wherein said apparatus further comprises an oxygen-containing gas source for supplying the oxygen-containing gas to the inner chamber.

3. An apparatus as defined by claim 1, wherein said apparatus further comprises a blower means for circulating the oxygen-containing gas and ozone within the inner chamber.

4. An apparatus as defined by claim 1, wherein said apparatus further comprises a movable support platform for supporting said object within said inner chamber.

5. An apparatus as defined by claim 1, wherein said reflective surface is a polished inner surface of said treatment tank.

6. An apparatus as defined by claim 1, wherein said reflective surface is provided by a reflective coating material applied to an inner surface of said treatment tank.

7. An apparatus as defined by claim 1, wherein said apparatus includes a plurality of reflective members mounted to an inner surface of said treatment tank, each reflective member providing one of said reflective surfaces.

8. An apparatus as defined by claim 1, wherein said apparatus includes a sensing means for sensing an ozone level within said inner chamber.

9. An apparatus as defined by claim 8, wherein said apparatus includes a control unit for controlling the operation of the apparatus in accordance with said ozone level sensed by the sensing means.

10. An apparatus as defined by claim 1, wherein said laser is an excimer laser.

11. An apparatus as defined by claim 10, wherein said excimer laser emits a laser beam of ultraviolet radiation having a wavelength of about 172 nm.

12. A method for treating an object with ozone, comprising:

placing the object within a sealed chamber containing an oxygen-containing gas;

introducing ultraviolet radiation into the chamber, whereupon exposure of the oxygen of the oxygen-containing gas to the ultraviolet radiation produces ozone gas; and reflecting the ultraviolet radiation at least twice within the chamber to transmit the ultraviolet radiation along a plurality of paths within the chamber, said plurality of paths avoiding contact with said object within the chamber.

13. A method as defined by claim 12, wherein said method further comprises:

circulating the ozone gas within the chamber.

14. A method as defined by claim 12, wherein said step of introducing ultraviolet radiation includes using a laser to produce a laser beam having a wavelength in the ultraviolet region of an electromagnetic spectrum.

15. A method as defined by claim 14, wherein said laser is an excimer laser.

16. A method as defined by claim 15, wherein said wavelength of said ultraviolet radiation is about 172 nm.

17. An apparatus as defined by claim 1, wherein at least one of said reflective surfaces provides diffuse reflection.

* * * * *